(12) United States Patent
Wang et al.

(10) Patent No.: US 11,584,940 B2
(45) Date of Patent: Feb. 21, 2023

(54) GEOMYCES MUTANT STRAIN AND APPLICATION THEREOF

(71) Applicant: Long Fang, Shangdong (CN)

(72) Inventors: Nengfei Wang, Shangdong (CN); Long Fang, Shangdong (CN)

(73) Assignee: Long Fang

( * ) Notice: Subject to any disclaimer, the term of this patent is extended or adjusted under 35 U.S.C. 154(b) by 0 days.

(21) Appl. No.: 16/759,928

(22) PCT Filed: Oct. 14, 2019

(86) PCT No.: PCT/CN2019/111010
§ 371 (c)(1),
(2) Date: Apr. 28, 2020

(87) PCT Pub. No.: WO2020/181765
PCT Pub. Date: Sep. 17, 2020

(65) Prior Publication Data
US 2021/0363549 A1    Nov. 25, 2021

(30) Foreign Application Priority Data
Mar. 13, 2019 (CN) ...................... 2019010186603.8

(51) Int. Cl.
*C12P 1/02* (2006.01)
*C12N 1/14* (2006.01)
(52) U.S. Cl.
CPC ................ *C12P 1/02* (2013.01); *C12N 1/145* (2021.05)

(58) Field of Classification Search
CPC ... C12P 1/02; C12N 1/145; C12N 1/14; A23L 5/46; C12R 2001/645
See application file for complete search history.

(56) References Cited

FOREIGN PATENT DOCUMENTS

CN    104804007 A  *  7/2015
CN    104804007 A     7/2015

OTHER PUBLICATIONS

Translation of CN 104804007 A (Year: 2015).*
Campbell, ColinK. ;Johnson, Elizabeth M.; Warnock, David W. (2013) .Identification of Pathogenic Fungi (Year: 2013).*
Campbell, ColinK. ;Johnson, Elizabeth M.; Warnock, David W. (2013) .Identification of Pathogenic Fungi (Year:2013) (Year: 2013).*
Wang, fengqin et al, (Identification of an Antarctic Fungus and Property Analysis of its Secretory Pigment), (Journal of Chinese Institute of Food Science and Technolog, 2013.

* cited by examiner

*Primary Examiner* — Louise W Humphrey
*Assistant Examiner* — Anjali Ajit Hirani

(57) ABSTRACT

A *Geomyces* mutant strain and an application thereof, relating to the technical field of the screening and application of functional microorganisms; the mutant strain is obtained through a mutagenic method, capable of greatly improving the yield of red pigment; the mutant strain has been preserved in the China Center for Type Culture Collection of Wuhan University on Jan. 24, 2019, and the preservation number is CCTCC NO: M2019086; the mutant strain can be widely used in the field of natural pigment production, can reduce the production cost of red pigment, and has a bright application prospect.

6 Claims, No Drawings

Specification includes a Sequence Listing.

GEOMYCES MUTANT STRAIN AND APPLICATION THEREOF

TECHNICAL FIELD

The present disclosure relates to the technical field of the screening and application of functional microorganisms, and more particularly, to a *Geomyces* mutant strain and an application thereof in pigment production.

BACKGROUND

Color is the first sensory index of food, affecting people's choice of food. Therefore, pigments are widely used in food-processing industry. According to different sources, edible pigments can be divided into natural pigments and synthetic pigments. As many synthetic pigments have been proven to be harmful to humans and are strictly restricted on their use in food, natural pigments are increasingly favored by food producers. Natural pigments are mainly divided into animal pigments, plant pigments, microbial pigments, and mineral pigments. At present, natural pigments account for 31% of the market share, lower than synthetic pigments that account for 40%. However, the market share of natural pigments is growing, and the market potential is huge (Mapari AS S, Thrane U, etc.).

Presently, most of the edible natural pigments approved by various countries come from animal and plant materials. However, the natural pigments from animals and plants are highly dependent on the raw materials, and the production scale is not easy to expand. Moreover, due to the differences in raw materials and climatic conditions, different batches of products differ greatly (Spears K), failing to meet the needs of the fast-growing food industry. In recent years, more and more researches have been devoted to finding natural pigments capable of replacing the aforesaid, and most of these researches focus on microbial pigments, especially fungal pigments. There are various fungal pigments, which are rich in color, safe and reliable, and possess functions of nutrition and health care. Moreover, they grow fast, are easy to cultivate, and can be simply produced on a large-scale. The utilization of fungal pigments has gradually become an important way to obtain natural pigments. For instance, *Monascus* red pigment produced by using *Monascus* has been widely adopted in East Asian countries. In 2006, the β-carotene produced by a Danish company by using Blakesleatrispora has obtained the food approval of the European Union (Wissgott U, Bortlik K). Using modern fermentation technology to produce fungal pigments achieves an easy control of conditions, a high degree of automation, and a large scale of production, which not only overcomes the aforesaid shortcomings, but save land resources and lower production costs.

In recent years, although China has made great progress in developing fungal resources, and has accumulated a certain amount of experience in using pigments, the resources of pigment-producing fungi are still relatively scarce. The fungal pigments capable of being industrialized are very few, far from meeting the modern food industry's demand for natural pigment production. Therefore, it is urgent to develop new species of pigment-producing fungi and improve their yield of pigment, thereby reducing the production cost of natural pigments and accelerating the promotion and use of natural pigments.

SUMMARY

The purpose of the present disclosure is to provide a *Geomyces* mutant strain and an application thereof. The mutant strain is obtained by adopting a mutagenic method, capable of reducing the production cost of natural pigments and accelerating the promotion and use of natural pigments.

The present disclosure provides a *Geomyces* mutant strain whose preservation number is CCTCC NO: M2019086.

The applicant of the present disclosure first selects a fungus that can produce yellow pigment and a high amount of red pigment from the soil of the Fildes Peninsula area, Antarctica. The selected fungus is identified as a *Geomyces* strain. To further improve its yield of red pigment, the strain is mutated by using atmospheric and room temperature plasma (ARTP) method, and a mutant strain with greatly improved yield of red pigment is screened out and named *Geomyces* sp.wnf-18C. The applicant has preserved the mutant strain *Geomyces* sp.wnf-18C in the China Center for Type Culture Collection of Wuhan University on Jan. 24, 2019, wherein the preservation number is CCTCC NO: M2019086.

The present disclosure also provides an application of the *Geomyces* strain in the fermentation production of red pigment.

The present disclosure also provides a fermentation method for producing red pigment, which takes the *Geomyces* strain as the fermentation strain.

In some embodiments of the present disclosure, the fermentation method comprises flask-shaking fermentation and fermenter fermentation.

In some embodiments of the present disclosure, the components and contents of the culture medium used in the fermentation method, respectively, are glucose 10 g/L and potato 200 g/L.

In some embodiments of the present disclosure, the temperature of the flask-shaking fermentation is 15° C., and the fermentation duration is 12 days.

In some embodiments of the present disclosure, the temperature of the fermenter fermentation is 15° C. and the fermentation duration is 12 days.

The present disclosure also provides an application of the *Geomyces* strain in the fermentation production of yellow pigment.

According to the present disclosure, a new *Geomyces* strain ST2 is screened out from the Antarctic soil sample, and its yield of red pigment is significantly higher than that of *Geomyces* sp.wnf-15A. On the 12th day of the flask-shaking fermentation, the $OD_{525}$ value of the supernatant of *Geomyces* sp.ST2 reaches 24.6, which is 26.1% higher than that of *Geomyces* sp.wnf-15A in the comparison group. To further improve its yield of red pigment, the strain is mutated by using the ARTP method, and a mutant strain with greatly improved yield of red pigment is screened out and named *Geomyces* sp.wnf-18C. On the 12th day of the flask-shaking fermentation of the mutant strain, the $OD_{525}$ value of the fermentation supernatant is as high as 33.6, which is 36.5% higher than that of the original strain ST2 and 72.3% higher than that of *Geomyces* sp.wnf-15A, achieving an unexpected technical effect.

Additionally, the quality of yellow pigment produced by the mutant strain *Geomyces* sp.wnf-18C is further improved. The color value of the yellow pigment produced by the mutant strain is 41, which is 7.8% higher than that of the original strain ST2, achieving an unexpected technical effect.

The mutant strain *Geomyces* sp.wnf-18C provided by the present disclosure can be widely used in the field of natural pigment production, can reduce the production cost of red pigment, and has a bright application prospect.

DETAILED DESCRIPTION OF THE DISCLOSURE

The present disclosure discloses a *Geomyces* mutant strain and an application thereof. Those skilled in the art can learn from the specification and realize the present disclosure through appropriately altering the technological parameters. It should be noted that all similar substitutions and modifications that are apparent to those skilled in the art are considered to fall into the scope of the present disclosure. The method and application of the present disclosure are described through preferred embodiments, and it is obvious that those skilled in the art can realize and apply the technology of the present disclosure through modifying, altering or combining the method and application described herein without departing from the content, spirit and scope of the present disclosure.

Those skilled in the art may, on the basis of the technical solution recorded in the present disclosure, adopt other conventional methods, experimental solutions and reagents in the field without being limited by the specific embodiments of the present disclosure.

The medium formula selected in the embodiments of the present disclosure is as follows:

PDA solid medium: potato 200 g, glucose 20 g, agar 15 g, and water 1000 ml;

PDA liquid medium: potato 200 g, glucose 10 g, and water 1000 ml.

Embodiment 1

Screening and Isolation of Red-Pigment-Producing Fungi.

Source of samples: soil samples collected from the Fildes Peninsula in the 34th Antarctic science investigation in 2018.

1. Screening Method:
(1) Preparation of Sample Diluent

Accurately weighing 10 g of soil sample, placing the 10 g of soil sample into a test tube containing 9 ml of sterile water, and oscillating to enable the sample to be sufficiently scattered, thereby preparing a 1:10 soil solution. Subsequently, taking 1 ml of soil solution and adding 9 ml of sterile water, thereby preparing a 1:100 soil solution; repeating the aforesaid step and preparing a 1:1000 soil diluent.

(2) Preliminary Screening of Strains

Taking 100 ul of the obtained soil diluent and uniformly coating it on a potato dextrose agar (PDA) culture medium plate, culturing for 3-4 days at a temperature of 15° C., observing bacterial colonies growing on the culture medium, and screening out fungal strains capable of producing red pigment.

(3) Secondary Screening of Strains

Placing single bacterial colonies capable of producing red pigment obtained from the preliminary screening on a new PDA culture medium by using an inoculation needle, culturing, and screening out colonies with larger ratio (HC value) of red circle diameter to colony diameter.

(4) Isolation and Purification of Strains

Inoculating the strains obtained from the secondary screening to a new PDA culture medium plate for streaking, culturing at a temperature of 15° C. for 3-4 days, observing the colonies growing on the culture medium, and repeating streaking for more than 3 times, wherein the monomorphic bacteria observed for several times under the microscope indicates that the strains have been isolated and purified.

Through the above steps, the applicant screens and obtains three purified strains of red-pigment-producing fungi, which are respectively named ST1, ST2 and ST3.

(5) Verification by Flask-Shaking Fermentation

Adding 7 ml of sterile water to a culture dish, respectively scraping the single colonies of ST1, ST2 and ST3 with an inoculation loop, rotating the culture dish, thereby making the bacteria on the plate fully distributed in the sterile water. Adding the bacterial suspension into a PDA liquid culture medium by using a pipette, and culturing for 12 days at a temperature of 15° C. and a speed of 120 r/min, wherein the inoculation amount is 10%. Centrifuging the fermentation liquid at a speed of 8000 r/min for 5 minutes, taking the supernatant and feeding it into a quartz cuvette with an optical path of 1 cm, and measuring the $OD_{525}$ value of the fermentation liquid by using a spectrophotometer, wherein the $OD_{525}$ value of the fermentation supernatant of ST2 is high, reaching 24.6, which indicates that the red pigment yield of ST2 in the three strains screened out by the applicant is high.

Embodiment 2

Identification of Red-Pigment-Producing Fungi.

The isolated and purified strain ST2 obtained from embodiment 1 is used for colony morphology and molecular biology identifications. The specific process is as follows:

1. Solid Plate Culturing

Inoculating strain ST2 on a PDA medium plate and culturing at 15° C. for 10 days, wherein the colony diameter is 8-12 mm.

Colony morphology: the bacterial colony of strain ST2 was white at the initial period and purple-red at the later period of growth. The shape is circular, the colony is flat and diffused, and the center is flat; the spore stem is short, the surface of the colony is in a floss shape or close to powder, and the spore is green-gray in the later period of growth. The initial period of the back of the colony is colorless, then becomes light yellow, and then becomes purple-red.

2. Molecular Biology Employs ITS Gene Identification

Scraping and collecting 100 mg of the mycelium of strain ST2 from the above PDA culture medium plate, and placing it in a 2 mL centrifugal tube containing glass beads; adding 750 μL of CTAB extracting solution (2% w/v CTAB, 1 mol/L NaCl, 0.1 mol/L Tris and 0.02 mol/L EDTA); placing the centrifugal tube in a Precellys 24 homogenizer for centrifugal grinding; transferring the liquid to a 1.5 mL centrifugal tube, adding 1.5 μL of thionyl ethanol, and water-bathing for 2 hours at a temperature of 65° C.; adding 750 μL of chloroform and iso-amyl alcohol (24:1 v/v), mixing upside down and centrifuging with a centrifugal force of 10000 g at room temperature for 15 minutes; collecting the upper-layer liquid and purifying by using a TaKaRa™ DNA fragment purification kit; storing the purified DNA at a temperature of −20° C.; amplifying the ITS sequence with a primer, wherein the conditions for the PCR reaction are: pre-degenerated at 94° C. for 5 minutes; at 94° C. for 30 seconds, at 55° C. for 30 seconds, at 72° C. for 1 minute; repeated for 30 circulations and extended at 72° C. for 10 minutes.

The ITS gene fragment obtained by the PCR amplification is sent to Shanghai Sunny Biotechnology Co., Ltd.[SM] for sequencing. The sequencing results show that the ITS gene sequence is SEQ ID NO: 1.

Through NCBI BLAST® comparative analysis, SEQ ID NO:1 has a high similarity (up to 98.2%) with SEQ ID NO:2 (GenBank: JN630629.1) derived from *Geomyces* sp.wnf-15A, which indicates that the strain ST2 screened out in the present invention is a *Geomyces* strain, and compared with *Geomyces* sp.wnf-15A, multiple nucleotide mutations occur in the strain ST2. The strain ST2 is named *Geomyces* sp.ST2 by the applicant.

1) Sequence of Geomyces sp.ST2
(SEQ ID NO: 1)

<u>gggg</u> <u>cctc</u> <u>cggt</u> <u>gatc</u> <u>gcct</u> gggt <u>tgcc</u> gcag gcct cccg ggta acct acca ccct ttgt ttat taca cttt gttg cttt ggca ggcc tgcc ctcg ggct gctg gctc cggc cggc gagc gctt gcca gagg acct aaac tctg tttg tcta tact gtct gagt acta tata atag ttaa aact ttca acaa cgga tctc ttgg ttct ggca tcga tgaa gaac gcag cgaa atgc gata agta atgt gaat tgca gaat tcag tgaa tcat cgaa tctt tgaa cgca catt gcgc cccc tggt attc cggg gggc atgc ctgt ccga gcgt catt acaa ccct caag ctca gctt ggta ttgg gccc cgcc gacc cggc gggc ccta aagt cagt ggcg gtgc cgtc cggc tccg agcg tagt aatt cttc tcgc tctg gagg tccg gtcg tgtg ctcg ccag caac cccc aatt tttt tcag gttg acct cgga tcag gtag ggat accc gctg aact taag cata tcaa taag cgga ggaa (2) Sequence of Geomyces sp.wnf-15A
(SEQ ID NO: 2)

<u>atca</u> <u>ttac</u> <u>agta</u> <u>gtcg</u> <u>cctg</u> ggt<u>t</u> <u>gccg</u> c<u>a</u>ag gcct cccg ggta acct acca ccct ttgt ttat taca cttt gttg cttt ggca ggcc tgcc ctcg ggct gctg gctc cggc cggc gagc gctt gcca gagg acct aaac tctg tttg tcta tact gtct gagt acta tata atag ttaa aact ttca acaa cgga tctc ttgg ttct ggca tcga tgaa gaac gcag cgaa atgc gata agta atgt gaat tgca gaat tcag tgaa tcat cgaa tctt tgaa cgca catt gcgc cccc tggt attc cggg gggc atgc ctgt ccga gcgt catt acaa ccct caag ctca gctt ggta ttgg gccc cgcc gacc cggc gggc ccta aagt cagt ggcg gtgc cgtc cggc tccg agcg tagt aatt cttc tcgc tctg gagg tccg gtcg tgtg ctcg ccag caac cccc aatt tttt tcag gttg acct cgga tcag gtag ggat accc gctg aact taag cata tcaa taag cgga ggaa Embodiment 3

Analysis of Red-Pigment-Producing Ability of *Geomyces* sp.ST2.
1. Flask-Shaking Fermentation
Adding the bacterial suspension of *Geomyces* sp.ST2 into a PDA liquid culture medium, wherein the inoculation amount is 10%; culturing for 12 days at a temperature of 15° C. and a speed of 120 r/min. Observing and recording the color change of the fermentation liquid at a fixed time every day. Taking a sample from the fermentation liquid, and centrifuging the fermentation liquid at a speed of 8000 r/min for 5 minutes. Taking the supernatant and feeding it into a quartz cuvette with an optical path of 1 cm, and measuring the $OD_{525}$ value of the fermentation liquid with a spectrophotometer. Meanwhile, the *Geomyces* sp.wnf-15A is taken as a comparison, and the results are shown in Table 1.

The observation results show that the fermentation liquid of *Geomyces* sp.ST2 turns red from the 4th day and purple red from the 5th day. As time goes, the purple red color of the fermentation liquid becomes darker and darker, and the mycelium concentration in the fermentation liquid is also higher and higher. Therefore, in the early stage of fermentation (72 h), *Geomyces* sp.ST2 mainly absorbs a lot of nutrients and stores pigment in the cell. From the 4th day, it secretes pigment out of the cell, and the fermentation liquid turns red. With the increase of mycelium concentration, the concentration of red pigment in the fermentation liquid also increases.

TABLE 1

Variation of $OD_{525}$ value of the *Geomyces* Fermentation Supernatant

| Time | *Geomyces* sp. wnf-15A | *Geomyces* sp. ST2 |
| --- | --- | --- |
| Day 1 | 0 | 0 |
| Day 2 | 0 | 0 |
| Day 3 | 0.1 | 0.2 |
| Day 4 | 1.6 | 2.4 |
| Day 5 | 5.1 | 6.8 |
| Day 6 | 8.4 | 11.8 |
| Day 7 | 12.9 | 14.3 |
| Day 8 | 14.1 | 18.2 |
| Day 9 | 16.7 | 21.7 |
| Day 10 | 18.1 | 23.5 |
| Day 11 | 18.9 | 24.1 |
| Day 12 | 19.5 | 24.6 |

From the data in Table 1, it can be seen that the $OD_{525}$ value of the fermentation supernatant of *Geomyces* sp.ST2 provided by the present disclosure is basically 0 within 72 hours of fermentation. By the 4th day, the $OD_{525}$ value increases to 2.4, and with the prolonging of fermentation time, the $OD_{525}$ value has been increasing; on the 12th day of fermentation, the $OD_{525}$ value of the supernatant of *Geomyces* sp.wnf-15A in the comparison group reaches 19.5, while the $OD_{525}$ value of the supernatant of *Geomyces* sp.ST2 reaches 24.6, which is 26.1% higher than that of the comparison group. Therefore, *Geomyces* sp.ST2 provided by the present disclosure can secrete a large amount of red pigment, and its yield of red pigment is significantly higher than that of *Geomyces* sp.wnf-15A, achieving an unexpected technical effect.

2. Fermentation in a Fermenter
Adding the bacterial suspension of *Geomyces* sp.ST2 into a PDA liquid culture medium, wherein the inoculation amount is 10%. culturing for 3.5 days at a temperature of 15° C. and a speed of 120 r/min, thereby obtaining a seed liquid.

Adding the PDA liquid medium and the defoamer to a 150 L fermenter, steam-sterilizing, cooling to 15° C., and then adding the seed liquid into the fermenter according to 10% inoculation amount, wherein the set fermentation parameters are: 15° C., 110 r/min, 50-100 LPM (air flow rate). Continuously fermentation-culturing for 12 days, taking a sample from the fermentation liquid, and centrifuging the fermentation liquid at a speed of 8000 r/min for 5 minutes.

Taking the supernatant and feeding it into a quartz cuvette with an optical path of 1 cm, and measuring the $OD_{525}$ value of the fermentation liquid with a spectrophotometer; meanwhile, taking *Geomyces* sp.wnf-15A as a comparison.

The results show that the $OD_{525}$ value of the supernatant of *Geomyces* sp.wnf-15A in the comparison group is only 16.7 after being continuously fermented in a 150 L fermenter for 12 days, while the $OD_{525}$ value of the supernatant of *Geomyces* sp.ST2 provided by the present disclosure is as high as 21.6, which is 29% higher than that of *Geomyces* sp.wnf-15A in the comparison group. Therefore, it is further proved that the red pigment yield of *Geomyces* sp.ST2 in the present disclosure is significantly higher than that of *Geomyces* sp.wnf-15A in the comparison group.

3. Extraction and Detection of Red Pigment

Feeding the fermentation liquid obtained from the above 150 L fermenter into a centrifuge bottle, and centrifuging for 15 minutes at a speed of 7500 r/min. Filtering the supernatant with a 200-mesh screen to remove the bacteria, thereby obtaining a pigment raw liquid;

Absorbing the pigment in the pigment raw liquid by using a DPH-722 macroporous adsorption resin, placing into chromatographic columns when reaching saturation adsorption, washing the two columns with water at a rate of 15 mL/min, eluting the pigment with 70% ethanol at the same speed, and collecting the eluent; rotary-evaporating the collected eluent to remove ethanol, and then obtaining the red pigment solid powder by vacuum freeze drying;

Weighing 0.1 g of red pigment solid powder, placing it into a 100 ml volumetric flask and fixing the volume; dissolving in an upside down manner, taking the diluent and feeding it into a quartz cuvette with an optical path of 1 cm. Measuring the absorbance A at the maximum wavelength (525 nm) by using a spectrophotometer, and calculating the color value.

Color value is one of the main quality indexes of natural pigment, which can reflect the level of pigment content and the coloring power of a product in a certain degree.

$$\text{Color value} = E_{1cm}^{1\%} 525 \text{ nm} = \frac{A}{C} \times \frac{1}{100},$$

wherein A is the absorbance of the tested sample solution, C is the concentration of the tested sample solution with g/ml as the unit, and 100 is the concentration conversion coefficient.

The results show that the $OD_{525}$ value of *Geomyces* sp.wnf-15A in the comparison group is 11.2, and the color value is 112, while the $OD_{525}$ value of *Geomyces* sp.ST2 provided by the present disclosure is 14.4, and the color value is 144, which is 30.9% higher than that of *Geomyces* sp.wnf-15A in the comparison group. Therefore, the quality of the red pigment produced by *Geomyces* sp.ST2 is better, achieving an unexpected technical effect.

Embodiment 4

Analysis of Yellow-Pigment-Producing Ability of *Geomyces* sp.ST2

Absorbing the pigment in the pigment raw liquid obtained in embodiment 2 by using a DPH-722 macro-porous adsorption resin, placing into chromatographic columns when reaching saturation adsorption, washing the two columns with water at a rate of 15 mL/min, eluting the pigment with 70% ethanol at the same speed, and collecting the eluent; rotary-evaporating the collected eluent to remove ethanol, and then obtaining the yellow-brown pigment solid powder by vacuum freeze-drying, namely, obtaining the yellow pigment, the powder of which is water soluble and can be used as a yellow colorant;

Weighing 0.1 g of yellow-brown pigment solid powder, placing it into a 100 ml volumetric flask and fixing the volume. Dissolving in an upside-down manner, taking the diluent and feeding it into a quartz cuvette with an optical path of 1 cm, and measuring the $OD_{440}$ value of the diluent.

The method for measuring the color value comprises: accurately weighing 0.1 g of yellow pigment solid sample, fixing the volume in a 100 ml volumetric flask. Measuring the absorbance A at the maximum wavelength (440 nm) by a cuvette with an optical path of 1 cm and calculating the color value.

$$\text{Color value} = E_{1cm}^{1\%} 440 \text{ nm} = \frac{A}{C} \times \frac{1}{100},$$

wherein A is the absorbance of the tested sample solution, C is the concentration of the tested sample solution with g/ml as the unit, and 100 is the concentration conversion coefficient.

The results show that the $OD_{440}$ value of the yellow pigment produced by *Geomyces* sp.ST2 provided by the present disclosure is 3.8, and the color value is 38.

Embodiment 5

ARTP Plasma Mutagenic Screening

The active particles in the plasma act on the microorganisms, which change the structure and permeability of microbial cell wall/membrane, cause gene damage, and then significantly change the microbial gene sequence and its metabolic network, resulting in microbial mutation. Compared with the traditional mutagenic method, ARTP method can effectively damage DNA diversity, achieve a high mutagenic rate and easily obtain mutant strains with good genetic stability.

The mutation caused by plasma mutation has a high randomicity, and the effect of mutation also has a high randomicity, which are difficult to predict. Therefore, in order to achieve the effective positive mutation, technicians usually need to carry out multiple rounds of mutation. The workload of screening is huge, and the possibility that the effective positive mutation cannot be achieved inevitably exists. However, as the plasma mutagenic method requires simple equipment, is easy to operate and can obtain a large number of mutants, it is a commonly-used mutagenic breeding method.

The applicant further uses *Geomyces* sp.ST2 as the original strain and carries out genetic transformation through ARTP plasma mutagenic method to further improve its yield of red pigment.

1. Mutagenic Method

Using 75% alcohol to clean the interior of the operation platform, turning on the ultraviolet lamp to irradiate, sterilizing for 20 minutes, and injecting helium (He) to preheat the machine before the mutation operation.

Taking out single colonies from a fresh culture dish, washing the single colonies by using 6-10 ml of sterile water in a scraping manner, transferring the bacterial suspension into a funnel through three layers of filter paper, filtering, collecting the filtrate by using a 50 ml triangular bottle, shaking up, and calculating the number of spores in 1 ml of suspension by using a blood cell counting plate; diluting the number of spores in the bacterial suspension to a number grade of $10^5$.

Setting parameters: the mutagenic device adopts high-purity helium (He) as the original gas to produce plasma, wherein the power supply is 100 W, the RF power is 13 W, the working distance is 4 mm, the plasma temperature is 28° C. and the gas flow is 10 slm; when the air flow and the radiation distance are set, the effect of ARTP on the sample depends on the length of irradiation duration; the exposure durations of spore suspension are respectively set as 10 s, 20 s, 30 s, 40 s, 50 s and 60 s; after different exposure durations, the numbers of spores are respectively measured and the death rates are respectively calculated; the specific results are shown in Table 2.

TABLE 2

Spore Death Rates Affected by Different Exposure Durations

| | Exposure Duration | | | | | |
|---|---|---|---|---|---|---|
| | 10 s | 20 s | 30 s | 40 s | 50 s | 60 s |
| Death Rate | 35.7% | 67.8% | 92.2% | 96.3% | 98.1% | 99.2% |

To sum up, the applicant takes 40 s as the exposure duration of the spore suspension.

2. Mutagenic Results

Taking out 100 μl of spore suspension after the mutagenic treatment, putting it on a PDA medium plate, coating evenly, culturing at a temperature of 15° C. until the colonies turn slightly red. Selecting out 102 single colonies that turn red, respectively placing them into the PDA liquid medium, culturing at a temperature of 15° C. and a speed of 120 r/min for 12 days in flask-shaking condition, and respectively measuring the $OD_{525}$ value of each strain's fermentation supernatant; meanwhile, taking the original *Geomyces* sp.ST2 as the comparison group.

The results show that none of the 102 mutant strains obtained in the first round of mutagenic screening has greater $OD_{525}$ value than that of the original strain, wherein the $OD_{525}$ values of 91 mutant strains are basically the same as that of the original strain, and the $OD_{525}$ values of the other 11 mutant strains are even 5-7% lower than that of the original strain.

The applicant continues carrying out 8 rounds of mutagenic screening by using the above method, and finally obtains a mutant strain whose $OD_{525}$ value of fermentation supernatant is significantly greater than that of the original strain, which is named *Geomyces* sp.wnf-18C by the applicant.

After culturing the mutant strain in the PDA liquid medium at a temperature of 15° C. and a speed of 120 r/min for 12 days in flask-shaking condition, the $OD_{525}$ value of the fermentation supernatant is as high as 33.6, which is 36.5% higher than that of the original strain and 72.3% higher than that of *Geomyces* sp.wnf-15A. The results show that the red pigment yield of the mutant strain *Geomyces* sp.wnf-18C is greatly increased, achieving an unexpected technical effect.

In addition, the applicant collects the yellow pigment in the fermentation supernatant of the mutant strain *Geomyces* sp.wnf-18C by using the method described in embodiment 3 and prepares the yellow pigment solid powder and measures its color value. The results show that the color value of the yellow pigment is 41, which is 7.8% higher than that of the original strain. Thus, the quality of the yellow pigment produced by the mutant strain *Geomyces* sp.wnf-18C is further improved and an unexpected technical effect is achieved.

The applicant has preserved the mutant strain *Geomyces* sp.wnf-18C in the China Center for Type Culture Collection ("CCTCC") of Wuhan University on Jan. 24, 2019, and the preservation number is CCTCC NO: M2019086. The CCTCC is located at the following address: College of Life Sciences, Wuhan University, Wuhan 430072 having a telephone number of (86-27) 6875 2319, (86-27) 6875 4052, (86-27) 6875 4533, and (86-27) 6875 4712.

What is claimed is:

1. A *Geomyces* strain that can secrete red pigment and yellow pigment out of the cell, wherein the *Geomyces* strain is known as *Geomyces* sp.wnf-18C and deposited at the China Center for Type Culture Collection of Wuhan University on Jan. 24, 2019, having a preservation number CCTCC NO: M2019086.

2. A fermentation method for producing a yellow and red pigment, the method comprising culturing the *Geomyces* strain of claim 1 in a culture medium that is a potato dextrose agar ("PDA") medium thus producing the yellow and red pigment.

3. The fermentation method of claim 2, wherein the fermentation method comprises flask-shaking fermentation.

4. The fermentation method of claim 3, wherein the PDA medium comprises glucose 10 g/L and potato 200 g/L.

5. The fermentation method of claim 3, wherein the temperature of the fermentation method is 15° C.

6. The fermentation method of claim 3, wherein the fermentation duration is 12 days.

* * * * *

SEQUENCE LISTING

```
<160> NUMBER OF SEQ ID NOS: 2

<210> SEQ ID NO 1
<211> LENGTH: 544
<212> TYPE: DNA
<213> ORGANISM: Geomyces sp.

<400> SEQUENCE: 1
ggggcctccg gtgatcgcct gggttgccgc aggcctcccg ggtaacctac caccctttgt     60
ttattacact ttgttgcttt ggcaggcctg ccctcgggct gctggctccg gccggcgagc    120
gcttgccaga ggacctaaac tctgtttgtc tatactgtct gagtactata taatagttaa    180
aactttcaac aacggatctc ttggttctgg catcgatgaa gaacgcagcg aaatgcgata    240
agtaatgtga attgcagaat tcagtgaatc atcgaatctt tgaacgcaca ttgcgccccc    300
tggtattccg gggggcatgc ctgtccgagc gtcattacaa ccctcaagct cagcttggta    360
ttgggccccg ccgacccggc gggccctaaa gtcagtggcg gtgccgtccg gctccgagcg    420
tagtaattct tctcgctctg gaggtccggt cgtgtgctcg ccagcaaccc ccaatttttt    480
tcaggttgac ctcggatcag gtagggatac ccgctgaact taagcatatc aataagcgga    540
ggaa                                                                 544
```

```
<210> SEQ ID NO 2
<211> LENGTH: 544
<212> TYPE: DNA
<213> ORGANISM: Geomyces sp.

<400> SEQUENCE: 2
atcattacag tagtcgcctg ggttgccgca aggcctcccg ggtaacctac caccctttgt      60
ttattacact ttgttgcttt ggcaggcctg ccctcgggct gctggctccg gccggcgagc     120
gcttgccaga ggacctaaac tctgtttgtc tatactgtct gagtactata taatagttaa     180
aactttcaac aacggatctc ttggttctgg catcgatgaa gaacgcagcg aaatgcgata     240
agtaatgtga attgcagaat tcagtgaatc atcgaatctt tgaacgcaca ttgcgccccc     300
tggtattccg gggggcatgc ctgtccgagc gtcattacaa ccctcaagct cagcttggta     360
ttgggccccg ccgacccggc gggccctaaa gtcagtggcg gtgccgtccg gctccgagcg     420
tagtaattct tctcgctctg gaggtccggt cgtgtgctcg ccagcaaccc ccaattttt     480 tcaggttgac ctcggatcag gtagggatac ccgctgaact taagcatatc aataagcgga     540
ggaa                                                                  544
```